United States Patent [19]

Slovak

[11] Patent Number: 4,790,319
[45] Date of Patent: Dec. 13, 1988

[54] STIMULATOR FOR HEMODIALYSIS
[75] Inventor: Petr Slovak, Prague, Czechoslovakia
[73] Assignee: Ceske vysoke uceni technicke v Praze, Prague, Czechoslovakia
[21] Appl. No.: 834,917
[22] Filed: Feb. 28, 1986

Related U.S. Application Data

[63] Continuation of Ser. No. 549,487, Nov. 4, 1983, abandoned, which is a continuation-in-part of Ser. No. 343,696, Jan. 28, 1982, abandoned.

[30] Foreign Application Priority Data

Jan. 28, 1981 [CS] Czechoslovakia .................. 624-81

[51] Int. Cl.⁴ ............................................. A61N 1/36
[52] U.S. Cl. ..................................... 128/419 R; 604/2
[58] Field of Search .................. 128/419 R, 421, 422; 604/20, 21

[56] References Cited

U.S. PATENT DOCUMENTS

| | | | |
|---|---|---|---|
| 3,064,641 | 11/1962 | Manenti et al. | 128/419 R |
| 3,894,532 | 7/1975 | Morey | 128/422 |
| 3,900,020 | 8/1975 | Lock | 128/422 |
| 3,918,459 | 11/1975 | Horn | 128/419 R |
| 3,954,111 | 5/1976 | Sato | 128/419 R |
| 4,052,978 | 10/1977 | Eugenio | 128/419 R |
| 4,055,190 | 10/1977 | Tany | 128/422 |
| 4,112,923 | 9/1978 | Tomecek | 128/419 R |

FOREIGN PATENT DOCUMENTS 2454816 12/1980 France .................. 128/421

OTHER PUBLICATIONS

Dodd et al, "Journal of Physics E.", vol. 7, No. 11, Nov. 74, pp. 897-901.

Primary Examiner—William E. Kamm
Attorney, Agent, or Firm—Klein & Vibber

[57] ABSTRACT

A stimulator which may be used to diminish the number of needed hemodialysis or peritoneal applications, as well as their duration. The stimulator is provided with at least two electrodes to be applied to a patient's body. The said electrodes are connected through an earphone and through a measuring instrument for indicating the average current quantity and its time derivative to the output of a generator of an electrical signal. The generator is fed from a direct current source. The stimulator may be applied separately, without an artificial kidney, viz. for diagnostical and therapeutical purposes in general medicine, or it may be used before hemodialysis or peritoneal dialysis.

4 Claims, 3 Drawing Sheets

STIMULATOR FOR HEMODIALYSIS

This application is a continuation of application Ser. No. 549,487, filed Nov. 4, 1983, now abandoned, which in turn is a continuation-in-part of application Ser. No. 343,696, filed Jan. 28, 1982, now abandoned.

This invention relates to a stimulator for hemodialysis, peritoneal dialysis, and for diagnostic and therapeutic use in general medicine.

Until now, when treating ailments by means of hemodialysis or peritoneal dialysis, there have been many difficulties, viz. a lengthy process of transmission of metabolic products from intracellular and extracellular spaces into a blood system, in the case of hemodialysis, and a lengthy process of transmission of said products into a dialysis solution, if it concerns peritoneal dialysis.

Other complications in hemodialysis and peritoneal dialysis are often polyneuritis, especially with diabetic patients. There may appear spasms of the legs and arms, and trembling, particularly with especially sensitive patients. Many difficulties heretofor encountered are usually obviated by means of chemical remedies. These remedies place an additional load upon the body of the patient who is already ill, and they cause an acceleration of the disruption of the patient's metabolism.

The above drawbacks are obviated by the stimulator for hemodialysis according to the invention. In accordance with the invention the stimulator is provided with at least two electrodes which are to be applied to the patient's body. At least one of the electrodes is connected to an earphone, then to an instrument measuring or indicating the current $I_{AV}$ and its time derivative, the current being supplied thereto by means of a generator. The generator is fed from direct current supply.

The principal advantage of the invention is in speeding up transmission of metabolic products from the tissue into the blood system or peritoneal space.

The stimulator limits amount of chemical drugs administered to the patient during dialysis complications.

The stimulator also speeds up restoration of dynamic balance of metabolic processes when applied transcutaneously to the tissue.

In order than the invention may be clearly understood and readily carried into effect, a preferred embodiment thereof is, by way of example, hereinafter more fully described and illustrated in the accompanying drawings, in which.

Figure 1:
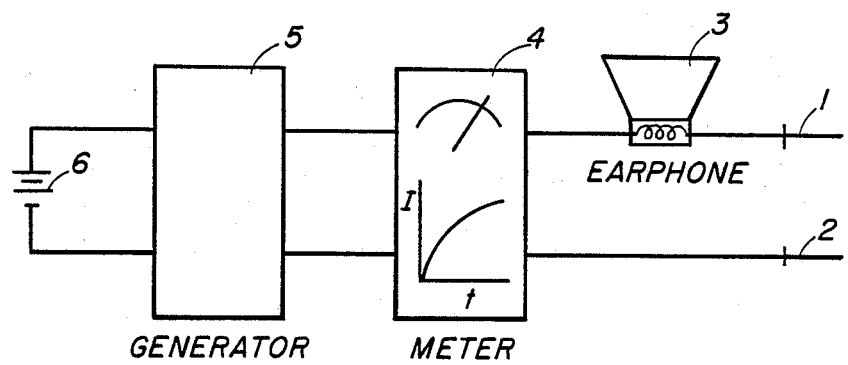
FIG. 1 is a block diagram of a stimulator for hemodialysis.

As shown in FIG. 1, two electrodes 1 and 2 are applied to the body of a patient (not shown) at two different predetermined locations, the electrode 1 being connected through an earphone 3 and through a measuring instrument 4 for measuring the average current and its time derivative supplied thereto from a signal generator 5. Generator 5 is fed from a direct current source 6, shown here as a battery. The electrodes 1 and 2 are made of metallic materials or of electrically conductive polymers. The earphone 3 indicates a conductive connection to the patient's body, and simultaneously, emits audible signals showing the fluctuations of the electric current.

The patient holds e.g. electrode 1 in his hand and electrode 2 is applied to swollen or painful areas or to places with small blood flow or along nerve and lymphatic paths indicated by doctor (all these points being on the body surface).

The measuring instrument 4 contains an ammeter, shown diagrammatically at the top of FIG. 1, and a current derivative measuring means shown at the bottom of FIG. 1. The measuring instrument may be conventional, provided with an analog output and a digital output for use with other devices, e.g. a programming unit of a hemodialyzing monitor, a plotter/recorder, oscilliscope or the like. Conventional timing and plotting means can be used to graph the average value of current $I_{AV}$ against time.

Figure 2:
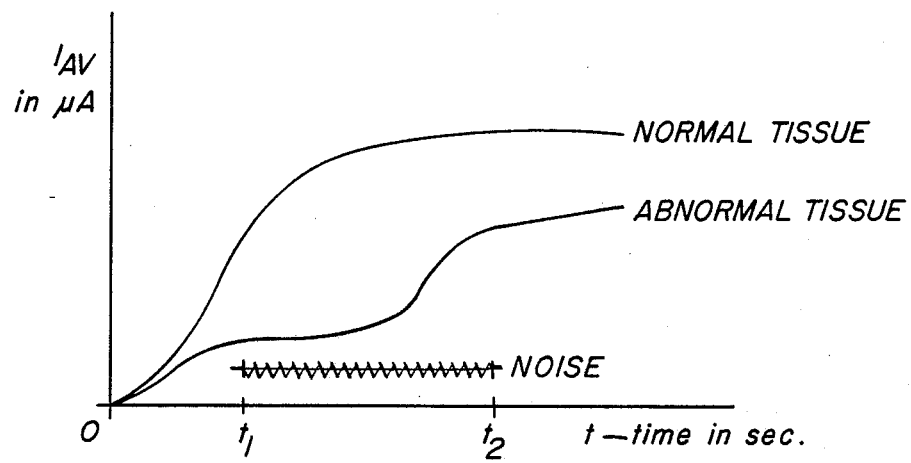
FIG. 2 shows average value of the current $I_{AV}$ in normal and abnormal tissue plotted against time of stimulation.

An example of average current $I_{AV}$ plotted against time (from the instant of application of electrode 2 to the patient's body) is shown in FIG. 2 illustrating normal tissue and abnormal tissue with local metabolic disturbances.

Small current fluctuations as shown in FIG. 2 (time interval $t_1-t_2$) can be detected in abnormal tissue e.g. by noise in earphone 3.

In FIG. 2 it can be seen that in a determined time the differences between normal and abnormal tissues consist not only of the differences between $I_{AV}$ values but also of the differences between time derivatives $(dI_{AV})/(d\,t)$ Meter 4 measuring the average value of the current and its time derivatives can be realized by usual means, in simplest case by a suitable Deprez D'Arsonval ammeter, which measures directly average value of the current and its time derivative is indicated by meter needle motion velocity. As mentioned above, conventional timing and plotting means can be used to graph a function of current versus time. From this graph, the time derivative of current can be computed either manually, or by conventional electronic computing means. Nevertheless, in many instances, the observed velocity of needle motion of the ammeter is sufficient to establish a rough estimate of the time derivative, being all that is necessary to distinguish normal from abnormal tissue and to thereby determine the appropriate duration of stimulation in one point.

The stimulation itself is carried out by consecutively applying electrode 2 to certain points on the skin in indicated body area. The stimulation is finished when all the points show identical stable values of current $I_{AV}$.

Figure 3:
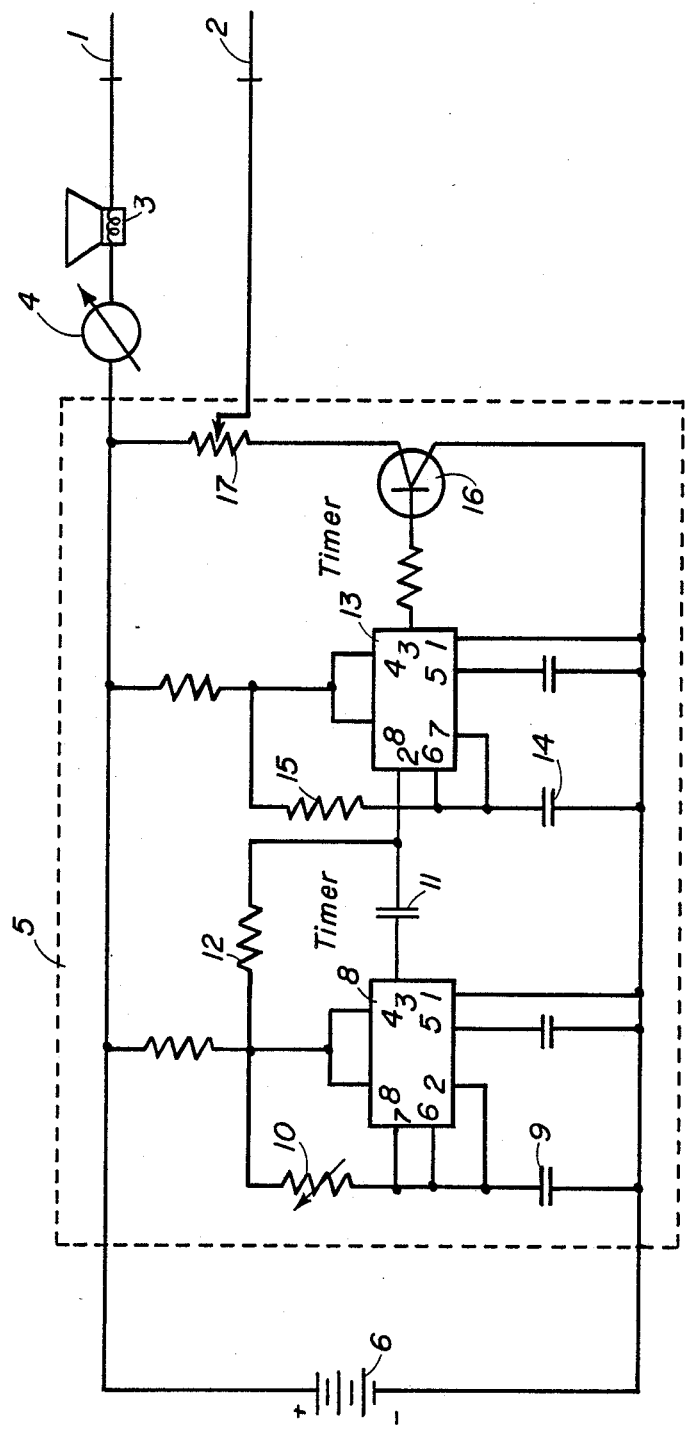
FIG. 3 is a circuit diagram of a preferred embodiment of stimulator for dialysis in accordance with the invention.

In FIG. 3 an example is shown of a circuit diagram of a simple stimulator for dialysis.

The generator 5 of the block diagram of FIG. 1 is there shown contained within a dash line outline. Generator 5 consists of a first timer 8, type 555, employed in an astable multivibrator. A charging capacitor 9 and an adjustable resistor 10 determine the frequency of the generated electrical pulses. Electrical pulses issue from an output of the timer 8 to an input of a second timer 13 through a derivation unit consisting of a capacitor 11 and a resistor 12. Timer 13, which is also type 555, is connected within the circuit of the monostable multivibrator. The width of the pulse of its output is determined by a capacitor 14 and a resistor 15; advantageously such width is a constant 100 usec. A transistor 16 is rendered conductive by pulses from the output of the timer 13. Connected in series with the collector of the transistor 16 is a potentiometer 17, one end of the winding of the potentiometer being connected to main wire 18, whereas the emitter of the transistor 16 is connected to the other main wire 19 of the generator. The sliding contact of the potentiometer 17 is connected e.g. to the electrode 2, and the other output of the potentiometer 17 is connected to the electrode 1 through the earphone 3 and the current measuring instrument 4.

In the above-described arrangement, the stimulator for dialysis operates with rectangular electrical pulses having frequencies in the range of 250 Hz to 5 kHz, such frequency being continuously adjustable by means of a variable resistor 10. The amplitude of the electrical pulses appliedf to the electrodes 1 and 2 is adjustable in the range of 0 to 17 V by means of the potentiometer 17. The battery 6 has an output of 18 V. The current measurement range of the measuring instrument 4 is 0 to 300 uA. The velocity of its hand motion the indicates the time derivative $(dI_{av})/(dt)$. The earphone 3 is of an electromagnetic type.

The stimulator is to be applied to a patient approximately one hour before hemodialysis or peritoneal dialysis.

The amplitude, polarity and frequency of the electrical pulses at the output of the stimulator are determined with respect to the necessary effect on the transcutaneously stimulated tissue of the patient.

The whole process of treatment of a patient with the stimulator before dialysis does not take more than 15 minutes.

It is advantageous to repeat the stimulation during hemodialysis or peritoneal dialysis in those spots on the patient's body where the tissue is soaked or where contractions and/or pains appear. Parameters of the stimulator are set up again so as to produce analgetic effects.

After the dialysis, e.g. after one hour, it is advantageous to carry out the stimulation in areas where painful symptoms appear. The polarity and shape of the electrical pulses produced by the generator 5 are to be determined so that analgetic effects may be produced by the apparatus.

The device according to the invention may also be applied for making diagnoses and for therapy in general medicine. When the stimulator is so used, the patient holds e.g. the electrode 1 in hand and the electrode 2 is used as an instrument for finding points of a low value of the electric current, viz. in the inspected area or along the paths of nerves, lymphatic ways, or muscle groups. In the point found, one applies the stimulator until the average value of the current reaches that of a healthy tissue.

Tissue permeability is affected by the said stimulator when curing idopathic swellings of limbs. Patients might stop taking sulfonamid diuretics, if the tissue stimulation is repeated every three to four months.

Although the invention is described and illustrated with reference to a single embodiment thereof, it is to be expressly understood that it is in no way limited to the disclosure of such preferred embodiment but is capable of numerous modifications within the scope of the appended claims.

I claim:

1. An electrical stimulator for a patient undergoing hemodialysis, comprising two electrodes to be applied to the body of the patient, and a circuit for energizing said electrodes, said circuit comprising a generator of an electric signal composed of electrical pulses in the range of 250 Hz to 5 KHz, a direct current source for energizing the generator, and output circuit means connected to the generator and to the electrodes, comprising an earphone for audibly indicating fluctuations in the current flowing in the output circuit means and means for indicating the average value of the current flowing in the output circuit means and means for measuring the time derivative $$(dI_{av})/(dt).$$

2. A stimulator in accordance with claim 1, wherein the electrical pulses are rectangular in configuration.

3. A stimulator in accordance with claim 1, comprising means for the continuous adjustment of the frequency of said electrical pulses.

4. An electrical stimulator for a patient undergoing hemodialysis, comprising two electrodes to be applied to the body of the patient, and a circuit for energizing said electrodes, said circuit comprising a generator of an electric signal composed of electrical pulses in the range of 250 Hz to 5 KHz, a direct current source for energizing the generator, and output circuit means connected to the generator and to the electrodes, comprising an earphone for audibly indicating fluctuations in the current flowing in the output circuit means, means for measuring the average value of the current flowing in the output circuit means and means for measuring the time derivative $$(dI_{av})/(dt).$$

* * * * *